United States Patent [19]

Madelmont et al.

[11] Patent Number: 5,001,158

[45] Date of Patent: Mar. 19, 1991

[54] NITROSOUREAS COMPOUNDS PREPARATION THEREOF AND UTILIZATION THEREOF IN ANTICANCEROUS

[75] Inventors: Jean-Claude Madelmont, Romagnat; Denise Godeneche, Chamalieres; Marie-France Moreau, Romagnat; Daniel Parry, Beaumont; Gustin Meyniel, Clerrint; Joël Oiry; Jean-Louis Imbach, both of Montpellier, all of France

[73] Assignee: Centre National de la Recherche Scientifique, Paris, France

[21] Appl. No.: 462,335

[22] Filed: Jan. 2, 1990

Related U.S. Application Data

[63] Continuation of Ser. No. 133,264, Dec. 16, 1987, abandoned, which is a continuation of Ser. No. 817,836, filed as PCT FR85/00080 on Apr. 10, 1985, published as WO85/04655 on Oct 24, 1985, abandoned.

[51] Int. Cl.$^5$ .................... C07C 275/68; A61K 31/17
[52] U.S. Cl. ........................................ 514/589; 564/33
[58] Field of Search ........................... 564/33; 514/589

[56] References Cited

FOREIGN PATENT DOCUMENTS

| | | | |
|---|---|---|---|
| 0021991 | 1/1981 | European Pat. Off. | 564/33 |
| 106123 | 4/1984 | European Pat. Off. | 564/33 |
| 7915672 | 1/1981 | France. | |
| 2528042 | 12/1983 | France. | |
| 2028795 | 3/1980 | United Kingdom | 514/589 |

OTHER PUBLICATIONS

Johnston et al, *J. of Med. Chem.*, vol. 14, No. 7 (1971), pp. 600–614.

Madelmont et al, *J. Med. Chem.*, 1985 28(9), 1346–50.

"Nitrosoureas in Cancer Treatment", B. Serrou, P. Schein and J. L. Imbach, Eds., 1981, 123.

J. Martinez, J. Oriy, J. L. Imbach et F. Winternitz, J. Med. Chem., 1982, 25, 178–182.

R. Maral et Coll. Eur. J. Med. Chem., Soumis Pour Publication (Reference p. 32 de la Demande de Brevet), 1984, 315–318.

French text "Mise a Jour 1986", Madelmont et al along with its English translation.

Primary Examiner—Carolyn S. Elmore
Attorney, Agent, or Firm—Handal & Morofsky

[57] ABSTRACT

Compounds having the general formula (I),

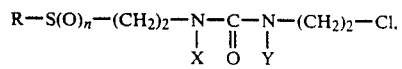

wherein X and Y represent individually H or —NO, at least one of them being a group-NO, n is 0, 1 or 2, R represents hydrogen, an aliphatic, cycloaliphatic, cycloaliphatic-alkyl, aryl or aralkyl radical, or a group of formula,

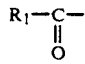

wherein $R_1$ is a lower alkyl radical or an aryl, all these radicals being optionally substituted. The present invention also relates to the compounds hereabove defined in the form of mixtures of their position isomers. Furthermore, the present invention discloses processes for preparing such compounds, as well as compositions, useful particularly in anticancerous chemotherapy, containing at least one of said compounds as an active principle.

4 Claims, 4 Drawing Sheets

NITROSOUREAS COMPOUNDS PREPARATION THEREOF AND UTILIZATION THEREOF IN ANTICANCEROUS

This application is a continuation of application Ser. No. 133,264, filed Dec. 16, 1987, which is a continuation of application Ser. No. 817,836, filed as PCT FR85/00080 on Apr. 10, 1985, published as WO85/04655 on Oct. 24, 1985, both now abandoned.

The present invention relates in general terms to new nitrosourea compounds, processes for their preparation and pharmaceutical compositions, based on such compounds, which are useful especially in murine anticancer chemotherapy.

More particularly, the present invention relates to compounds with oncostatic activity against leukemia strain L1210 which are derived from cysteamine and belong to the class of the chloroethylnitrosoureas.

The chloroethylnitrosoureas represent a class of compounds used in anticancer chemotherapy for the treatment of glioblastomas in Hodgkin's disease and gastrointestinal cancers.

The most widely used chloroethylnitrosoureas are 1-3 bis (2-chloroethyl)-1-nitrosourea (BCNU), 1-(C2-Chloroethyl)-3-cyclohexyl-1-nitrosourea (CCNU) and 1-(2-chloroethyl)-3-(4-methyl cyclohexyl)-1-nitrosourea (methyl-CCNU). Of the numerous derivatives in this series which have recently been prepared throughout the world, some have been selected for phase I and II clinical trials on the basis of their broad spectrum of action on murine tumors. These are:

chlorozotocin, 1-(2-chloroethyl) 3-[(4-amino 2-methyl pyrimidine-5 yl)-methyl]-1-nitrosourea (ACNU), 1-(2-hydroxyethyl)-3-(2-chloroethyl) 3-nitrosourea (HECNU), 1-(2-chloroethyl)-3-[1'-(5'-p nitrobenzoyl 2', 3'-isopropylidene) alpha beta D-ribofuranosyl]-1-nitrosourea (RFCNU), and N[N-(2-chloroethyl) N-nitrosocarbamoyl]-N'-[N(2-chloroethyl) carbamoyl] N'-nitrosocystamine (CNCC).

In this series, CNCC seems to be the most promising substance, as indicated in Table 1.

In fact, from the trials whose results are collated in this table, it seems that CNCC possesses a very valuable activity, both qualitatively and quantitatively. It is found to be active against all the types of tumor listed in Table I, with the exception of fibrosarcoma I.C.I.G. This activity is quantitatively greater than those observed with the other chloroethylnitrosoureas.

TABLE I

| | Increase in the survival time (I.L.S.: T/C × 100)[1] (i.p. treatment on days 1, 5 and 9) | | | | |
|---|---|---|---|---|---|
| TUMOR | CHLOROZOTOCIN 15 mg/kg i.p. | R.P.C.N.U. 15 mg/kg i.p. | R.F.C.N.U. 20 mg/kg i.p. | H.E.C.N.U. 10 mg/kg i.p. | C.N.C.C. 30 mg/kg i.p. |
| Leukemia L 1210 (grafted intracutaneously) | N.S. | N.S. | 167 | ∞ | ∞ |
| Lewis pulmonary carcinoma (implanted subcutaneously) | N.S. | N.S. | N.S. | ∞ | ∞ |
| Melanocarcinoma B 16 (implanted subcutaneously) | N.S. | 151 | 144 | 198 | 200 |
| Glioma 26 (implanted subcutaneously) | N.S. | 127 | N.S. | 182 | 200 |
| Mammary adenocarcinoma TM2 (implanted subcutaneously) | N.S. | 134 | N.S. | 165 | 185 |
| Fibrosarcoma I.C.I.G. C1 (implanted subcutaneously) | ∞ | | ∞ | N.S. | N.S. |
| Carcinoma of the colon (colon 26) (implanted subcutaneously) | ∞ | N.S. | N.S. | ∞ | ∞ |
| Ovarian M 555 (implanted subcutaneously) | ∞ | ∞ | N.S. | 210 | >254 |

N.S. - Not significant: ∞ = 50% more of the treated animals are cured
[1]Taken from "Nitrosoureas in Cancer Treatment", Ed. B. Serrou, P.S. Schein and J.L. Imbach, Elsevier North Holland, 1981, 132.

Finally, it is pointed out that CNCC is employed in larger doses (30 mg/kg) than those at which chlorozotocin, 1-(2-chloroethyl)-3-[(2'-3'-4° tri o acetyl) alpha beta D-ribopyrannosyl]-1-nitrosourea (RPCNU), R.F.C.N.U. or H.E.C.N.U. is used, which is an additional asset in anticancer chemotherapy. In this field, one is very much aware of the need to find a compromise between an effective dose of product, making it possible to achieve the maximum regression of the tumor, and the minimum of adverse side-effects.

CNCC therefore possesses a broad spectrum of action and permits a more effective treatment of murine tumors.

It is for this reason that the present invention relates to new cytostatic agents derived from CNCC which have an improved activity compared with the products of the prior art and/or a different spectrum of action.

The said cytostatic agents are compounds of the general formula I:

in which:

X and Y are individually defined as H or —NO, at least one being an —NO group, n is equal to 0, 1 or 2, and R Is hydrogen, an aliphatic, cycloaliphatic, cycloaliphatic-alkyl, aryl or aralkyl radical or alternatively a group in which $R_1$ is a lower alkyl or aryl radical,
all these radicals being optionally substituted.

Aliphatic radicals are understood as meaning linear or branched alkyl, alkenyl or alkynyl radicals containing from 1 to 8 carbon atoms. Preference is given to lower alkyl radicals, i.e. alkyl radicals containing from 1 to 7 carbon atoms, more particularly $C_1$ to $C_3$ radicals such as methyl and ethyl.

Cycloaliphatic radicals are understood as meaning saturated or unsaturated radicals containing 3 to 8 carbon atoms. The cyclohexyl radical is preferred in particular.

Aryl radicals are understood as meaning $C_6$–$C_{30}$ radicals containing one or more substituted or unsubstituted nuclei, for example of the benzene type. Among these radicals, preference is given in particular to the phenyl radical optionally substituted by an —$NO_2$ group, for example the group:

$$\langle\bigcirc\rangle-NO_2.$$

A cycloaliphatic-alkyl radical is understood as meaning a lower alkyl radical substituted by one or more cycloaliphatic radicals. Likewise, an aralkyl radical is understood as meaning a lower alkyl radical substituted by one or more aryl radicals. The terms "lower alkyl", "cycloaliphatic" and "aryl" are employed as defined above. Among these radicals, the trityl radical $((C_6H_5)_3$—C—$)$ is especially preferred.

Among the compounds according to the invention, preference is given in particular to the derivatives of the formula II:

$$R-S(O)_n-(CH_2)_2-NH-\underset{\underset{O}{\parallel}}{C}-\underset{\underset{NO}{|}}{N}-(CH_2)_2-Cl$$

in which the —NO group is carried by the nitrogen nearer the chlorine.

The following must be mentioned among the most valuable compounds according to the invention:

$$H-S-(CH_2)_2-NH-\underset{\underset{O}{\parallel}}{C}-\underset{\underset{NO}{|}}{N}-(CH_2)_2-Cl$$

N—[N-(2-chloroethyl)-N-nitrosocarbamoyl]cysteamine $$CH_3-S-(CH_2)_2-NH-\underset{\underset{O}{\parallel}}{C}-\underset{\underset{NO}{|}}{N}-(CH_2)_2-Cl$$

S-methyl-N—[N-(2-chloroethyl)-N-nitrosocarbamoyl]cysteamine.

$$CH_3-S-(CH_2)_2-\underset{\underset{NO}{|}}{N}-\underset{\underset{O}{\parallel}}{C}-NH-(CH_2)_2-Cl$$

S-methyl-N-nitroso-N—[N-(2-chloroethyl)carbamoyl]cysteamine.

$$CH_3-\underset{\underset{O}{\parallel}}{C}-S-(CH_2)_2-NH-\underset{\underset{O}{\parallel}}{C}-\underset{\underset{NO}{|}}{N}-(CH_2)_2-Cl$$

S-acetyl-N—[N-(2-chloroethyl)-N-nitrosocarbamoyal]cysteamine.

$$O_2N-\langle\bigcirc\rangle-\underset{\underset{O}{\parallel}}{C}-S-(CH_2)_2-NH-\underset{\underset{O}{\parallel}}{C}-\underset{\underset{NO}{|}}{N}-(CH_2)_2-Cl$$

S-paranitrobenzoyl-N—[N-(2-chloroethyl)-N-nitrosocarbamoyal]cysteamine.

$$(C_6H_5)_3-C-S-(CH_2)_2-NH-\underset{\underset{O}{\parallel}}{C}-\underset{\underset{NO}{|}}{N}-(CH_2)_2-Cl$$

S-trityl-N—[N-(2-chloroethyl)-N-nitrosocarbamoyl]cysteamine.

The present invention also relates to the sulfoxides of the formula:

$$R-\underset{\underset{O}{\parallel}}{S}-(CH_2)_2-\underset{X}{\overset{|}{N}}-\underset{\underset{O}{\parallel}}{C}-\underset{Y}{\overset{|}{N}}-(CH_2)_2-Cl$$

and the sulfones of the formula:

$$R-\underset{\underset{O}{\parallel}}{\overset{\overset{O}{\parallel}}{S}}-(CH_2)_2-\underset{X}{\overset{|}{N}}-\underset{\underset{O}{\parallel}}{C}-\underset{Y}{\overset{|}{N}}-(CH_2)_2-Cl$$

corresponding to the controlled or complete oxidation of the sulfur in the cysteamine derivatives of the formula:

$$R-S-(CH_2)_2-\underset{X}{\overset{|}{N}}-\underset{\underset{O}{\parallel}}{C}-\underset{Y}{\overset{|}{N}}-(CH_2)_2-Cl$$

The invention further relates to isomeric mixtures of the compounds of the general formula I:

$$R-S(O)_n-(CH_2)_2-\underset{X}{\overset{|}{N}}-\underset{\underset{O}{\parallel}}{C}-\underset{Y}{\overset{|}{N}}-(CH_2)_2-Cl,$$

taking into account the fact that if X and Y have different meanings—when one is hydrogen and the other the —NO group—two position isomers are obtained according to whether —NO is carried by the nitrogen nearer the chlorine or the nitrogen nearer the sulfur.

In particular, the invention relates to the following mixture of position isomers:

$$\begin{cases} CH_3-S(O)_n-(CH_2)_2-\underset{NO}{\overset{|}{N}}-\underset{\overset{\parallel}{O}}{C}-NH-(CH_2)_2-Cl \\ CH_3-S(O)_n-(CH_2)_2-NH-\underset{\overset{\parallel}{O}}{C}-\underset{NO}{\overset{|}{N}}-(CH_2)_2-Cl \end{cases}$$

The compounds according to the present invention can be prepared by different processes.

The compounds in which R is a hydrogen or an aliphatic, cycloaliphatic, cycloaliphatic-alkyl, aryl or aralkyl radical and n=0 can be prepared by nitrosation of the corresponding compound of the formula:

$$R-S-CH_2-CH_2-NH-\underset{\overset{\parallel}{O}}{C}-NH-CH_2-CH_2Cl$$

by reaction with an alkali metal nitrite or alkaline earth metal nitrite in the presence of an organic acid, in particular by reaction with $NaNO_2$ in formic acid.

Figure 1:
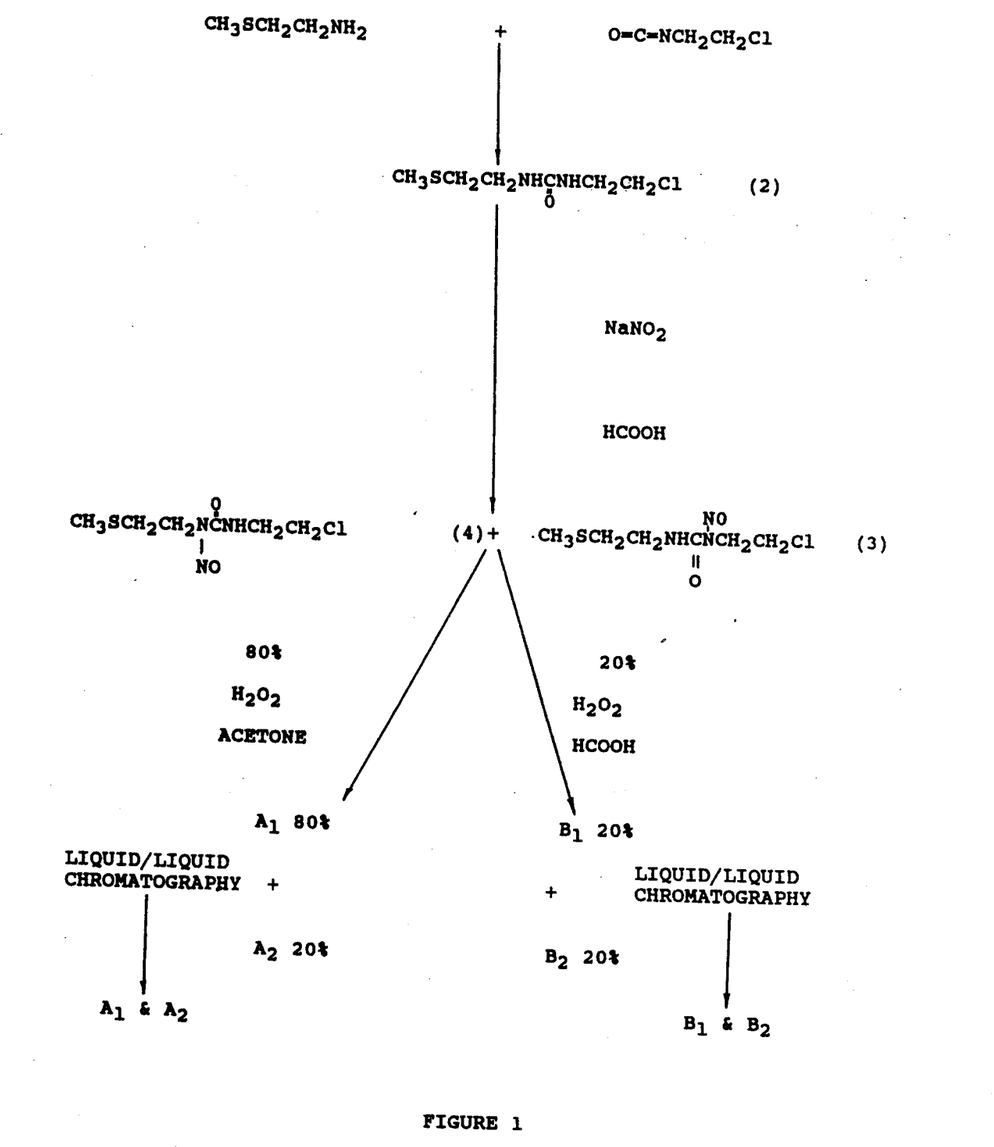

In particular, scheme I shown in FIG. 1, illustrates a process for the preparation of the compounds of the formula:

in which R is $-CH_3$.

The urea (2) is prepared by reacting S-methylcysteamine with chloroethyl isocyanate. The urea (2) obtained is then nitrosated with $NaNO_2$ in the presence of formic acid to give a mixture consisting of the following two position isomers: S-methyl-N-[N-(2-chloroethyl)-N-nitrosocarbamoyl] cysteamine (3) and S-methyl-N-nitroso [N-(2-chloroethyl)-N-carbamoyl]cysteamine (4).

Analysis of the NMR spectrum of this mixture shows the presence of these two isomers, one nitrosated nearer the chlorine (3) and the other nitrosated nearer the sulfur (4), in proportions of 25%/75%.

As these two isomers are very difficult to separate, a pure product will preferably be obtained using the following process, which consists in reacting $H_2N-CH_2-CH_2Cl$ with in which $X_1$ is an activating group, to give the derivative nitrosated nearer the sulfur, or in reacting $R-S-CH_2-CH_2-NH_2$ with in which $X_2$ is an activating group, to give the derivative nitrosated nearer the chlorine.

An activating group $X_1$ or $X_2$ is understood as meaning any functional group which favors the addition of the nitrosated reactant, such as a nitrosocarbamate, onto the primary amine group of the ethylamines:

so as to prepare the chloroethylnitrosourea compounds according to the invention, respectively nitrosated nearer the sulfur or nearer the chlorine. French Patent no. 2 487 343 mentions the activating groups conventionally used for this purpose; p-nitrophenyl, is mentioned in particular.

Figure 2:
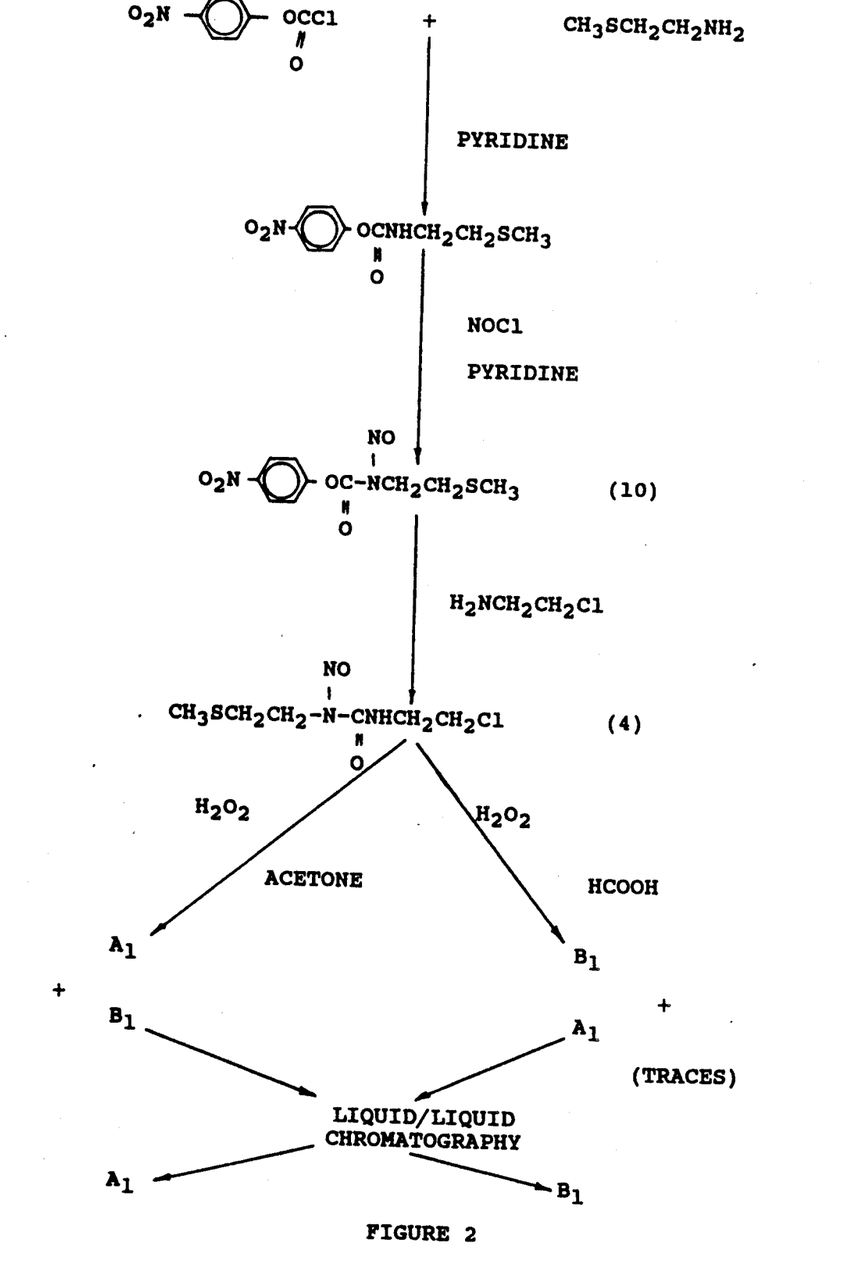
Figure 3:
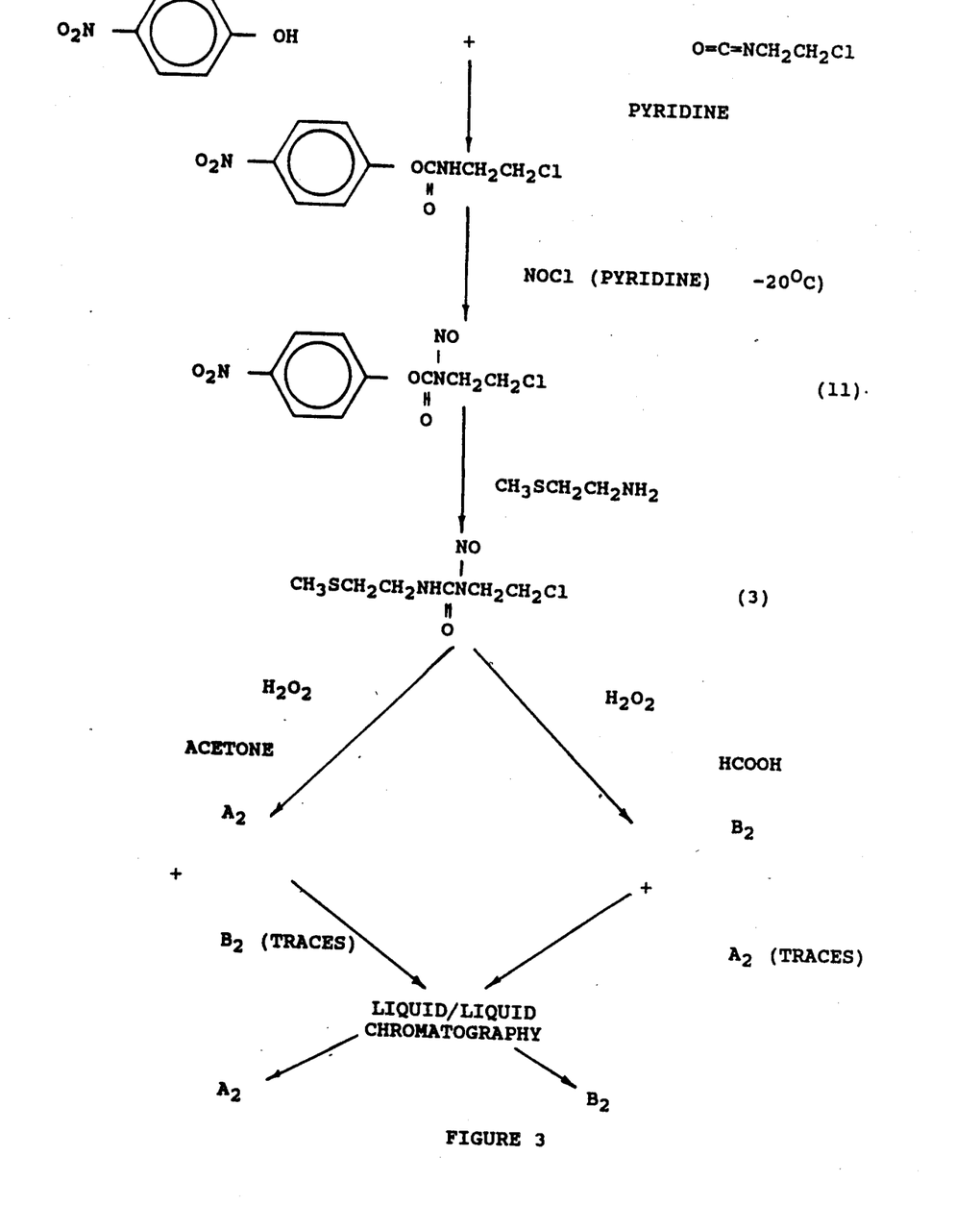

Schemes II and III shown in FIGS. 2 and 3 respectively illustrate processes for the preparation of the compounds according to the invention, in the pure state and not as a mixture.

Scheme II relates to a process for the preparation of S-methyl-N-nitroso[N-(2-chloroethyl)-N-carbamoyl] cysteamine (4). This pure compound (4) is obtained by the addition of the nitrosocarbamate (10), the end of which constitutes the activating group $X_1$, onto 2-chloroethylamine, $H_2NCH_2CH_2Cl$, making it possible to obtain the chloroethylnitrosourea derivative (4) nitrosated nearer the sulfur.

Scheme III relates to a process for the preparation of the position isomer of the previous compound (4) i.e. S-methyl-N-N-(2-chloroethyl)-N-nitrosocarbamoyl] cysteamine (3). This is done by the addition of the nitrosocarbamate (11) onto S-methylcysteamine, the of the nitrosocarbamate corresponding in this case to an activating group $X_2$, making it possible to obtain the chloroethylnitrosourea derivative (3) nitrosated nearer the chlorine.

The preferred method for obtaining a compound in which R is and $n=0$ will be to carry out the thioesterification of a compound of the formula:

with a reactive derivative of the corresponding acid for example the acid chloride.

This thioesterification will be carried out under the conditions normally employed by those skilled in the art, for example in the presence of an anhydrous solvent such as pyridine. It is illustrated by the last step of scheme II.

Figure 4:
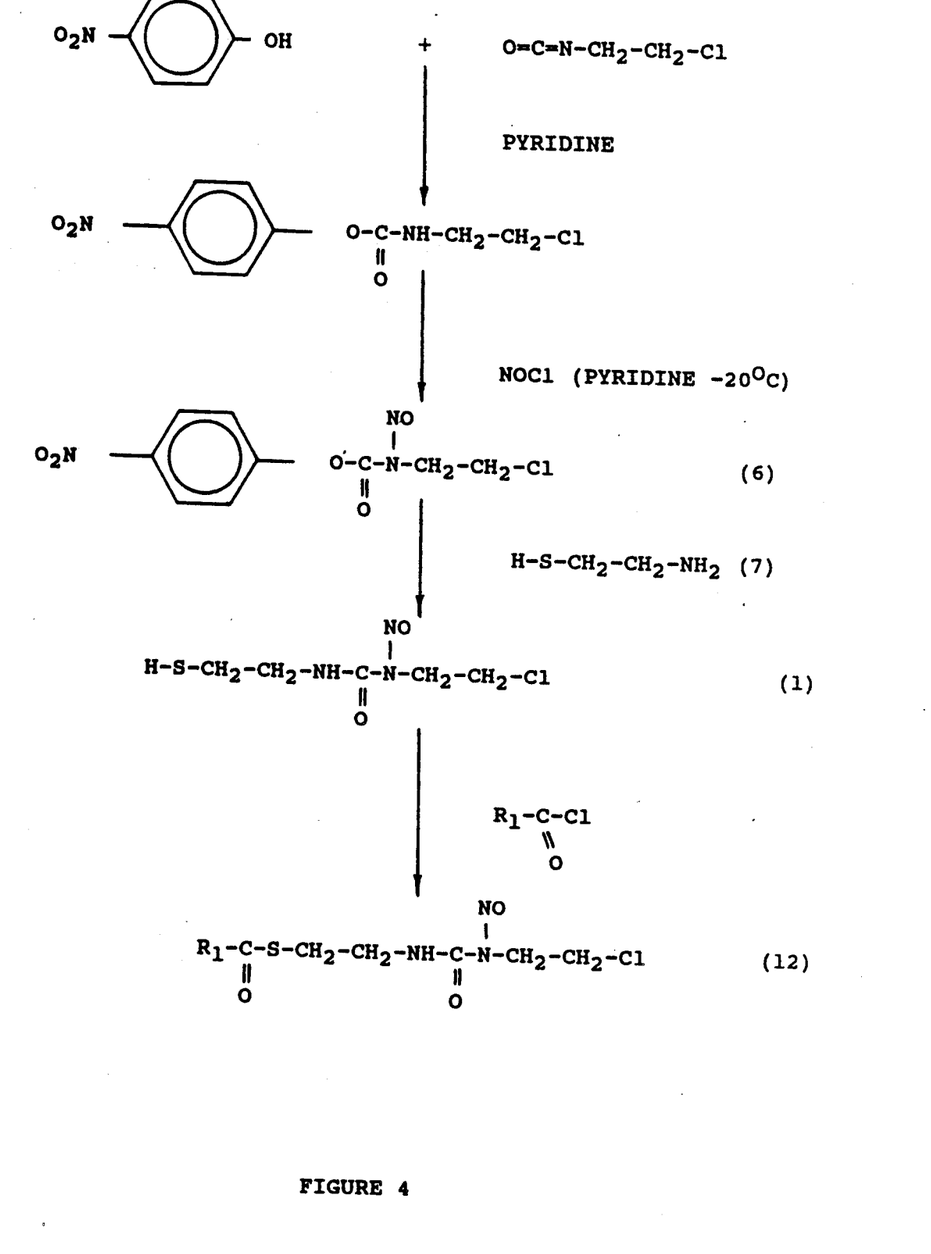

Scheme IV shown in FIG. 4 relates to a process for the preparation of N-N-(2-chloroethyl)-N-nitrosocarbamoyl]cysteamine (1) by the addition of the N-(2-chloroethyl)-N-nitrosocarbamate of paranitrophenol (6) onto cysteamine (7). As previously, the reactant (6) constitutes the compound carrying an activating group $X_2$ making it possible to obtain a derivative nitrosated nearer the chlorine. However, it will be necessary for this reaction to be carried out under a stream of inert gas, for example nitrogen, because the thiol (1) tends to dimerize to form CNCC.

The last step of scheme IV corresponds to the preparation of the compounds of the general formula I in which n=0 and R is

The chloroethylnitrosourea compound (1) obtained is then reacted with the acid chloride corresponding to the final product (12) which it is desired to prepare.

The oxidized compounds according to the invention, namely sulfoxides (n=1) and sulfones (n=2), can be prepared by the controlled or complete oxidation of the sulfur in the corresponding compounds (n=0) with a peroxide such as hydrogen peroxide.

To obtain the sulfoxides of the formula:

according to the invention, the corresponding compounds of the formula:

are reacted with a peroxide such as hydrogen peroxide, in the presence of acetone, with stirring.

To obtain the sulfones of the formula:

according to the invention, the corresponding compounds of the formula:

are likewise reacted with a peroxide such as hydrogen peroxide, in the presence of formic acid, with stirring.

The synthesis of the compounds according to the invention in the form of sulfoxides and sulfones is represented by the last steps in schemes I, II and III.

For the sake of simplicity, the following conventions will be used hereafter:

the letter A denotes the compounds according to the invention in the form of sulfoxides and the letter B denotes those in the form of sulfones;

the index 1 refers to the compounds nitrosated nearer the sulfur, in particular S-methyl-N-nitroso[N-(2-chloroethyl)-N-carbamoyl]cysteamine, and the index 2 relates to the compounds nitrosated nearer the chlorine, in particular S-methyl-N-N-(2-chloroethyl)-N-nitrosocarbamoyl] cysteamine.

The sulfoxides ($A_1$ and $A_2$) and sulfones ($B_1$ and $B_2$) obtained, as well as their mixtures, are purified in the conventional manner by chromatography, especially by liquid/liquid chromatography.

Moreover, as the compounds according to the invention have an oncostatic activity, the present invention further relates to pharmaceutical compositions containing at least one of the said compounds as the active principle.

Such compositions will advantageously be used in anticancer chemotherapy.

In view of the broad spectrum of action of the compounds according to the invention, the pharmaceutical compositions in which they are present may be used for the treatment of circulating tumors such as leukemia, or solid tumors such as, for example: melanocarcinoma, pulmonary carcinoma, carcinoma of the colon, mammary adenocarcinoma, glioma or fibrosarcoma.

Compositions of this type may be administered parenterally, for instance intravenously, or orally.

They may be in the form of tablets, capsules, solutions or suspensions in non-toxic aqueous or organic media, dispersible powders or solutions or suspensions in injectable non-toxic aqueous or organic media.

Finally, these compositions will be administered at doses of between 10 mg and 100 mg of active principle/day. For each treatment, the dose will be determined inter alia according to the type of tumor, the state of the patient and the toxicity of the product.

The examples which follow will make it possible to demonstrate further characteristics and advantages of the present invention.

EXAMPLE 1

Preparation of a mixture of
S-methyl-N-[N-(2-chloroethyl)-N-nitrosocarbamoyl)]
cysteamine and
S-methyl-N-[N-(2-chloroethyl)-N-carbamoy)]-N-nitrosocysteamine Scheme I)

A—(a) Preparation of
S-methyl-N-[N-(2-chloroethyl)-N-carbamoyl]
cysteamine

An equimolecular mixture of 50 mmol of S-methylcysteamine and chloroethyl isocyanate in 100 cm³ of anhydrous ether is stirred for 12 hours at room temperature.

After 1 hour of stirring, the clear solution becomes turbid. After 12 hours, the copious white precipitate is filtered off and rinsed with ether. The product obtained can be used as such for the following reactions:

Yield: 80%.

Melting point: 74%.

TLC: 5% EtOH/CHCl$_3$, silica: Merck Sl 60 F 2154.

Rf: 0.5.

IR: (KBr)ν cm⁻¹: 3320 (NH), 2900 to 3000 (CH), 1630

1570, 1520 (NH—C=O)

NMR (CDCl₃)δ ppm [2.06 s (3) CH₃S], [2.60 t (2) —SCH₂CH₂],

[3.36 m (2)—SCH₂CH₂], [3.4 to 3.6 m (4) NHCH₂CH₂Cl], [5.23 to 5.9 m (2) NH]

(b) Nitrosation of S-methyl-N-[N-(2-chloroethyl)-N-carbamoyl]cysteamine 40 mmol of the urea obtained under (a) are solubilized in 100 cm³ of a formic acid/water mixture (70/30 vol/vol). The solution is cooled to 0° C. and 400 mmol of sodium nitrite are added in small portions over 1 hour, the temperature being monitored. The solution is stirred for 1 hour at 0° C. after the addition of NaNO₂ has ended.

The reaction medium is diluted with 100 cm³ of iced water and then extracted with chloroform (5 times 50 cm³) and the extract is dried rapidly and then concentrated under reduced pressure.

The liquid product can either be used as such or purified to remove the degradation substances (in low proportions of 3 to 4%) by liquid-liquid chromatography on a silica column: eluent CH₂Cl₂.

Determination of the two isomers by HPLC gives the proportions 80/20 for derivative with NO nearer chlorine/derivative with NO nearer chlorine (sic). Yield: 90%

B—This mixture can also be prepared by the following process (a) S-Methyl-N-]N-(2-chloroethyl-N-carbamoyl]-cysteamine (Scheme I)

A solution of 1.82 g (20 mmol) of S-methylcysteamine in 40 cm³ of methylene chloride is stirred at 0° C. and 1.71 ml (20 mmol) of 2-chloroethyl isocyanate are added dropwise over 15 minutes.

The mixture is then left to return to room temperature. The reaction, which is followed by TLC, is complete in 4 hours. The solution is then evaporated to dryness in vacuo and the powder obtained is crystallized from a methylene chloride/ether mixture (v/v). 3.2 g (81%) of S-methyl-N-[N-(2-chloroethyl)-N-carbamoyl]cysteamine are collected.

TLC: (eluent: chloroform/methanol 8.5/1.5).
Rf=0.5 - iodine vapor detection.
Melting point=80° C.

| Calculated % | C 36.64 | H 6.61 | N 14.24 |
| Found % | 36.41 | 6.84 | 14.30 |

NMR spectrum ¹H (DMSO d₆)δ ppm: NH: (m) centered at 6.22; 2 H; exchangeable with D₂O, CH₂Cl: (m) centered at 3.56: 2 H, CH₂NH: (m) ranging from 3.42 to 3.05; 4 H; this multiplet is modified after exchange of the NH groups S—CH₂: (t) centered at 2.48; 2 H, CH₃: (s) 2.04; 3 H, (b) Nitrosation of S-methyl-N-[N-(2-chloroethyl)N-carbamoyl]cysteamine A solution of 1.47 g (7.5 mmol) of the compound obtained under a) in 15 cm³ of formic acid is stirred in a bath of iced water. Nitrosation is then carried out by adding 1.55 g (22.5 mmol) of sodium nitrite over 30 minutes. The mixture is left to return to room temperature and stirring is continued for 1 hour. The yellow solution is then treated with 70 cm³ of iced water to encourage a yellow gum to deposit in the medium. This gum is extracted with 2×50 cm³ of methylene chloride. The combined organic phases are washed with distilled water (2×10 cm³) and then dried over sodium sulfate and evaporated to dryness in vacuo. The yellow oil collected is subsequently purified on a silica column (Kieselgel 60, 70-230 mesh) using an eluting mixture consisting of methylene chloride and petroleum ether (v/v). This gives 1.43 g of an isomeric mixture of S-methyl-N-[N-(2-chloroethyl)-N-nitrosocarbamoyl]cysteamine. and S-methyl-N-nitroso-N-[N-(2-chloroethyl)-N-carbamoyl]cysteamine.

TLC (eluent=methylene chloride) Rf=0.4, UV and iodine vapor detection.

| Analysis | C₆H₁₂SN₃O₂Cl (225.5) | | |
|---|---|---|---|
| Calculated % | C 31.92 | H 5.32 | N 18.62 |
| Found % | 32.16 | 5.59 | 18.47 |

NMR spectrum ¹H (DMSO d₆)δ ppm:
NH: (m) centered at 8.91; 1 H; exchangeable with D₂O, ( m) centered at 4.0; 2 H, CH₂—Cl; CH₂—NH: (m) ranging from 3.85 to 3.36; 4 H; part of this multiplet is modified after exchange of the NH, S—CH₂ belonging to the molecule nitrosated nearer the chlorine: (t) centered at 2.67, S—CH₂ belonging to the molecule nitrosated nearer the sulfur: (t) centered at 2.48, These two triplets of S—CH₂ integrate like two protons. The ratio of the relative integrations of these two protons gives proportions of 25% for the isomer nitrosated nearer the chlorine and 75% for the isomer nitrosated nearer the sulfur.

CH₃ belonging to the molecule nitrosated nearer the chlorine: (s) 2.10.

CH₃ belonging to the molecule nitrosated nearer the sulfur: (s) 2.05.

These two CH₃ singlets integrate like 3 protons in the same proportions as above.

EXAMPLE 2

N-[N-(2-Chloroethyl)-N-nitrosocarbamoyl]cysteamine (Scheme IV)

A solution of 1.15 g (15 mmol) of freshly sublimed cysteamine (Fluka) in 90 cm³ of anhydrous benzene is stirred at room temperature, under a stream of nitrogen, and 4 g (14.6 mmol) of the N-(2-chloroethyl)-N-nitrosocarbamate of paranitrophenol are added in small portions (the addition takes place over 1 hour).

The reaction, which is followed by TLC, is complete in 12 hours.

The reaction mixture is then evaporated to dryness under reduced pressure. The residual yellow oil is subsequently chromatographed on a dry silica column (Kieselgel 60, 70-230 mesh, Merck) with methylene chloride as the eluent. 1.3 g of product are collected in the form of an oil at room temperature. If kept in a refrigerator and under a nitrogen atmosphere, this oil crystallizes.

TLC (eluent: methylene chloride) Rf=0.30—UV and iodine vapor detection.

| Analysis | $C_5H_{10}SN_3O_2Cl$ (211.5) | | |
|---|---|---|---|
| Calculated % | C 28.36 | H 4.72 | N 19.85 |
| Found % | 28.29 | 4.74 | 19.72 |

IR spectrum (film)$\nu$ cm$^{-1}$ (NH) 3380; (CH$_2$) 2980, 2940; (SH) 2580; (C=O) 1720; (amide) 1525: (N—NO) 1490.

NMR spectrum $^1$H (CDCl$_3$)$\delta$ ppm:

NH: (m) centered at 7.36; 1 H; exchangeable with D$_2$O.

(t) centered at 4.18; 2 H

NH—CH$_2$ and CH$_2$Cl: (m) ranging from 3.80 to 3.42; 4 H; part of this multiplet is modified after exchange of the NH.

S—CH$_2$: (m) centered at 2.83; 2 H; this multiplet is modified after exchange of the SH.

SH: (t) centered at 1.47; 1 H; exchangeable with D$_2$O.

Oxidation of the compound with iodine in methanol solution gave a quantitative yield of the dimer dinitrosated nearer the chlorine, which is the minority isomer of CNCC: bis-N,N'-[N-(2-chloroethyl)-N-nitrosocarbamoyl]cystamine, a compound which has already been described by two other methods of synthesis (French Patent no. 79 15672—J. OIRY, J. L. IMBACH).

"Nitrosoureas in Cancer Treatment", B. SERROU, P. SCHEIN and J. L. IMBACH, Eds., Elsevier/North Holland, New York, J. L. IMBACH, J. MARTINEZ, J. OIRY, CH. BOURUT, E. CHENU, R. MARAL and C. MATHE, 1981, 123.

J. MARTINEZ, J. OIRY, J. L. IMBACH and F. WINTERNITZ, J. Med. Chem., 1982, 25, 178.

EXAMPLE 3

S-Acetyl-N-[N-(2-chloroethyl)-N-nitrosocarbamoyl]-cysteamine (Scheme IV)

A solution of 1.060 g (5 mmol) of N-[N-(2-chloroethyl)-N-nitrosocarbamoyl]cysteamine, obtained in Example 2, in 10 cm$^3$ of freshly distilled pyridine is stirred at 0° C., under a stream of nitrogen, and 0.71 cm$^3$ (10 mmol) of freshly distilled acetyl chloride is added dropwise. The reaction medium is kept at 0° C. for 1 hour and then left to return to room temperature. The solution, which is followed by TLC., is complete in 12 hours. The solution is then poured into 100 cm$^3$ of iced water to encourage a gum to deposit. This gum is taken up with 2×50 cm$^3$ of methylene chloride. The combined organic phases are then washed with distilled water (4×50 cm$^3$), dried over sodium sulfate and then evaporated to dryness in vacuo. 1.250 g of a slightly yellow, oily product are collected. This oil is subsequently purified by chromatography on a silica column (Kieselgel 60, 70-230 mesh, Merck) using methylene chloride as the eluent. The S-acetylated derivative is collected with a yield of 70%, i.e. 0.880 g.

TLC (eluent: methylene chloride): Rf=0.2—UV and iodine vapor detection. Crystallizes from a mixture of methylene chloride and petroleum ether (2/8).

Melting point=62-64° C.

| Analysis | $C_7H_{12}SN_3O_3Cl$ (253.5) | | |
|---|---|---|---|
| Calculated % | C 33.13 | H 4.73 | N 16.56 |
| Found % | 33.26 | 4.70 | 16.46 |

IR spectrum (KBr)$\nu$ cm$^{-1}$: (NH) 3360; (CH$_2$) 3040, 2960; absence of (SH) band at 2580; (C=O) 1720, 1675; (amide) 1520: (N—NO) 1480.

NMR spectrum $^1$H (CDCl$_3$)$\delta$ ppm: NH: (m) centered at 7.27; 1 H; exchangeable with D$_2$O, (t) centered at 4.19; 2 H, NH—CH$_2$: (m) centered at 3.70; 2 H; this multiplet is modified after exchange of the NH, CH$_2$Cl: (t) centered at 3.52; 2 H, S—CH$_2$: (t) centered at 3.16: 2 H, (s) 2.38: 3 H.

EXAMPLE 4

S-Paranitrobenzoyl-N-[N-(2-chloroethyl)-N-nitresocarbamoyl]

cysteamine (Scheme IV)

The method used is identical to that employed in Example 3. In this case, the acetyl chloride is replaced with paranitrobenzoyl chloride.

The compound is again purified by chromatography on a silica column with methylene chloride as the eluent. Yield=70%.

TLC (eluent: methylene chloride): Rf=0.3—UV and iodine vapor detection.

Crystallizes from a mixture of methylene chloride and petroleum ether (2/8). Melting point=85-86° C.

| Analysis | $C_{12}H_{13}SN_4O_5Cl$ (360.5) | | |
|---|---|---|---|
| Calculated % | C 39.94 | H 3.60 | N 15.53 |
| Found % | 39.83 | 3.64 | 15.49 |

IR spectrum (KBr)$\nu$ cm$^{-1}$: (NH) 3400; (CH), (CH$_2$) 3120, 3080, 3050, 2980, 2940, 2870; absence of (SH) band at 2580; (C=O) 1720, 1650; (amide) 1515; (N—NO) 1480.

NMR spectrum $^1$H (CDCl$_3$)$\delta$ ppm: aromatic protons: (m) centered at 8.20; 4 H, NH : (m) centered at 7.28; 1 H; exchangeable with D$_2$O (t) centered at 4.18; 2 H, NH—CH$_2$ (m) centered at 3.83; 2 H; this multiplet is modified after exchange of the NH, CH$_2$Cl and S—CH$_2$: (m) ranging from 3.60 to 3.32; 4 H.

EXAMPLE 5

S-Trityl-N-[N-(2-chloroethyl)-N-nitrosocarbamoyl]-cysteamine

The method used is identical to that used in Example 2. In this case, the starting material is S-tritylcysteamine (prepared according to F. I. CARROL, H. M. DICKSON and M. E. WALL, J. Org. Chem., 1965, 30, 33) and the solvent used is ethyl acetate. The compound is purified by chromatography on a silica column using an eluting mixture consisting of ether and petroleum ether (1/9). Yield=68%.

TLC (eluent: ethyl acetate/petroleum ether (1/4) Rf= 0.5—UV and iodine vapor detection.

Crystallizes from a mixture of ether and petroleum ether (¼). Melting point=112–113° C.

| Analysis | C$_{24}$H$_{24}$SN$_3$O$_2$Cl (453.5) | | |
|---|---|---|---|
| Calculated % | C 63.50 | H 5.29 | N 9.26 |
| Found % | 63.86 | 5.27 | 9.38 |

IR spectrum (KBr)ν cm$^{-1}$: (NH) 3340; (CH), (CH$_2$) 3060, 3020, 2960, 2940; (C=O) 1720, 1690; (amide) 1520; (N—NO) 1490.

NMR spectrum $^1$H (CDCl$_3$)δ ppm: aromatic protons: (m) centered at 7.30; 15 H, NH: (m) centered at 6.90; 1 H; exchangeable with D$_2$O, (t) centered at 4.10; 2 H, CH$_2$NH and CH$_2$Cl: (m) ranging from 3.60 to 3.04; 4 H; part of this multiplet is modified after exchange of the NH, S—CH$_2$: (t) centered at 2.51; 2 H.

EXAMPLE 6

Preparation of S-methyl-N-nitroso-N-N-(2-chloroethyl)-N-carbamoyl]cysteamine (Scheme 11)

The carbamate is prepared by reacting paranitrophenyl chloroformate (100 mmol) with S-methylcysteamine (100 mmol) in pyridine at room temperature. After a reaction time of 12 hours, the mixture is poured all at once onto ice and the precipitate obtained is filtered off, washed with iced water and dried in a vacuum desiccator over P$_2$O$_5$. Yield 60%.

Nitrosation is carried out with nitrosyl chloride in pyridine at −20° C. by the processes described in the literature . After a reaction time of 4 hours at −20° C., the medium is hydrolyzed with iced water and extracted with chloroform and the organic phase is treated with hydrochloric acid, dried over MgSO$_4$ and then distilled under reduced pressure. This gives an oil which can be used for the remainder of the reaction.

yield 80%. J. Martinez, J. Oiry, J. L. Imbach and F. Winternitz, J. Méd. Chem., 25, 178–182, 1982.

A solution of 2-chloroethylamine (40 mmol), freed from its hydrochloride with triethylamine, is added dropwise to a solution of 20 mmol of nitrosocarbamate in 25 cm$^3$ of DMF.

The course of the reaction is followed by TLC on Merck Si 60 F 254 silica, eluent CHCl$_3$. The reaction has ended after 30 minutes. The solvent is distilled under reduced pressure and the residue is deposited on a silica column. Elution is carried out with chloroform or methylene chloride. The title product, eluted in the top fractions, is an oil. Yield=70%.

TLC, Merck Si 60 F 254, eluent CHCl$_3$, Rf: 0.40

IR: window (KBr)ν cm$^{-1}$: 3350 (NH), 2900 to 3000 (CH), 1710

1520 (NH—C=O), 1480 (N—NO).
NMR: CDCl$_3$,δ ppm:
[2.10 s (3) CH$_3$S, 2.46 t

[3.66 to 3.83 m (4) NHCH$_2$CH$_2$Cl], [4.00 t

[7 to 7.60 m (1) NHCH$_2$CH$_2$Cl exchangeable]

EXAMPLE 7

S-Methyl-N-(2-chloroethyl)-N-nitrosocarbamoyl]cysteamine (Scheme III)

The corresponding carbamate and nitrosocarbamate are prepared by the processes in the literature (idem previous references), adapted to the case of 4-nitrophenol.

20 mmol of S-methylcysteamine are added dropwise, with stirring, to a cooled solution of 20 mmol of nitrosocarbamate in 30 cm$^3$ of THF. Stirring is continued for 1 hour at this temperature.

The progress of the reaction is monitored by TLC (silica: Merck Si 60 F 254, eluent CHCl$_3$). The reaction has ended after 1 hour. The reaction medium is concentrated in vacuo, deposited on a silica column and eluted with CH$_2$Cl$_2$ or CHCl$_3$ to separate the p-nitrophenol from the CNU (3).

The product, eluted with the top fractions, is an oil. Yield: 90%.

TLC: Merck Si 60 F 254, eluent CHCl$_3$, Rf=0.40 :
IR: KBr (ν cm$^{-1}$): 3350 (NH), 2900 to 3000 (CH), 1715

1520 (NH—C=O), 1480 (N—NO).
NMR: CDCl$_3$,δ ppm:
[2.13 s (3) CH$_3$S], [2.73 t (2) SCH$_2$CH$_2$NH], [3.43 m (2)

[3.70 m (2) SCH₂CH₂NH], [4.10 t

[7 to 7.50 m (1) SCH₂CH₂NH exchangeable].

S-Methyl-N-N-(2-chloroethyl)-N-nitrosocarbamoyl-cysteamine can also be prepared in the following manner:

A solution of 1.179 g of approximately 90% pure 2-methylthioethylamine or S-methylcysteamine (Fluka) in 50 cm³ of anhydrous benzene is stirred at 20° C., under a stream of nitrogen, and 2.98 g (10.9 mmol) of the N-(2-chloroethyl)-N-nitrosocarbamate of paranitrophenol are added in small portions. (The addition takes place over 1 hour and the reaction is exothermic, the reaction mixture being kept at 20° C. in a bath of cold water.) The reaction, which is followed by TLC, is complete in three hours. The solution is then evaporated to dryness under reduced pressure and the residual oil obtained is chromatographed on a silica column (Kieselgel 60, 70–230 mesh, Merck) with an eluting mixture consisting of methylene chloride and petroleum ether (v/v). 1.85 g of a yellow oil are collected and this is subsequently kept under nitrogen in a refrigerator.

TLC (eluent: methylene chloride) Rf=0.40—UV and iodine vapor detection.

| Analysis | C₆H₁₂SN₃O₂Cl (225.5) | | |
|---|---|---|---|
| Calculated % | C 31.92 | H 5.32 | N 18.62 |
| Found % | 32.04 | 5.27 | 18.49 |

IR spectrum (film)ν cm⁻¹: (NH) 3360; (CH₂) 2960, 2920, 2840; (C=O) 1720; (amide) 1520; (N—NO) 1490.

NMR spectrum ¹H (CDCl₃)δ ppm: NH: (m) centered at 7.43; 1 H; exchangeable with D₂O, (t) centered at 4.13; 2 H, NH—CH₂: (m) centered at 3.67: 2 H: this multiplet is modified after exchange of the NH, CH₂Cl: (t) centered at 3.47; 2 H, S—CH₂: (t) centered at 2.73; 2 H, CH₃—S: (s) 2.10; 3 H.

EXAMPLE 8

Preparation of the sulfoxides of the mixture of Example 1 (Scheme I)

A1

A2

15 cm³ of 110 v. H₂O₂ are added to an acetone solution of 15 mmol of isomeric mixture, cooled to 0° C.

The resulting mixture is stirred for 1 hour and the progress of the reaction is monitored by TLC.

When the reaction has ended, the mixture is diluted with H₂O (30 cm³) and extracted with chloroform, the extract is dried and the solvent is distilled under reduced pressure.

The product is deposited on a silica column and chromatographed with a 0% to 2% gradient of ethanol in chloroform.

7.5 mmol of sulfoxide (A1), 4 mmol of mixture and 1 mmol of sulfoxide (A2) are isolated.

Melting points: A1=73° C., A2=107° C.

TLC: silica: Merck Si 60 F 254, eluent 5% EtOH/CHCl₃, Rf A1=0.30, Rf A2=0.25.

IR: (KBr)ν cm⁻¹ A1: 3220 (NH), 2900–3000 (CH), 1480 (N—NO), 1030 (S=O) A2: 3220 (NH), 2900–3000 (CH), 1480 (N—NO), 1045 (S=O).

NMR: CDCl₃, δ ppm: A1 [2.60 s (3) CH₃S], [2.80 t

[3.60 to 3.90 m (4) NH-CH₂CH₂Cl], [4.20 t

[7.60 to 8 m (1) NHCH₂CH₂Cl exchangeable], A2 [2.60 s (3) CH₃S], [3.00 t (2) SCH₂CH₂NH],

[3.86 m (2) SCH₂CH₂NH],

[7.40 to 7.60 m (1) S—CH₂CH₂NH exchangeable]

Mass spectrum A₁ m/z: 136 [CH₃—SO—CH₂CH₂N=N—OH]⁺·, m/z: 105, 107 [CO—N—CH₂CH₂Cl]⁺·, m/z: 92 [m/z 136—(N—NO)]⁺, m/z: 78 [CH₃SOH—CH₂]⁺·, m/z: 64 [CH₃SOH]⁺·; A2 m/z: 134 [CH₃SOCH₂CH₂NH—C≡O]⁺, m/z: 91 [CH₃SOCH₂CH₂]⁺, m/z: 63, 65 [CH₂CH₂Cl]⁺, m/z: 64 [CH₃SOH]⁺·.

EXAMPLE 9

Preparation of the sulfones of the mixture of Example 1

The experimental protocol is the same as previously for the sulfoxides, using formic acid instead of acetone.

20 cm$^3$ of formic acid and 20 cm$^3$ of 110 v. hydrogen peroxide are used for 15 mmol of isomeric mixture.

The separation and extraction are performed in the same manner, elution being carried out with a 0% to 1% gradient of ethanol in chloroform.

The same quantities of pure compounds and mixture are isolated as the experiment of Example 3.

| Melting points | B1 | 72-76° C. |
|---|---|---|
| | B2 | 94-97° C. |

TLC: silica: Merck Si 60 F 254, eluent 5% EtOH/CHCl$_3$,
RF B1: 0.55, RF B2: 0.50
IR: (KBr)$\nu$ cm$^{-1}$ B1: 3300 (NH), 2900 to 3000 (CH), 1710

1520 (NHCO), 1485 (N—NO), 1130 (O=S=O) B2: 3350 (NH), 2910 to 3000 (CH), 1420 (N—NO), 1125 (O=S=O)
NMR: CDCl$_3$, δ ppm: B1[2.93 s (3) CH$_3$S], [3.10 t

[3.66 to 3.90 m (4) HNCH$_2$CH$_2$Cl], [4.20 m

[7.10 to 7.33 m (1) HNCH$_2$CH$_2$Cl exchangeable]. B2 [3.60 s CH$_3$—S], [3.26 to 3.66 m (4) SCH$_2$CH$_2$NH and 3.83 to 4.33 m (4) S—CH$_2$CH$_2$NH and NCH$_2$CH$_2$Cl], [7.33 to 7.66 m (1) SCH$_2$CH$_2$NH exchangeable].
Mass spectrum B1 m/z: 152 [CH$_3$SO$_2$CH$_2$CH$_2$N=N—OH]$^+$·, m/z 105, 107 [CONCH$_2$CH$_2$Cl], m/z: 108 [m/z 136—(N—NO)]$^+$·, m/z: 94 [CH$_3$SO$_2$HCH$_2$]$^+$·, m/z: 80 ]CH$_3$SO$_2$H]$^+$·, B2 m/z: 150 [CH$_3$SO$_2$CH$_2$CH$_2$NH—C=O]$^+$, m/z: 107 [CH$_3$SO$_2$CH$_2$CH$_2$]$^+$·, m/z: 80 [CH$_2$SO$_2$H]$^+$·, m/z: 63, 65 [CH$_2$CH$_2$Cl]$^+$.

EXAMPLE 10

By following the procedure described in Examples 8 and 9, starting from the compounds obtained in Examples 6 and 7, the corresponding sulfoxides and sulfones A1/A2/B1/B2 are obtained in the pure form after liquid/liquid chromatography.

The Rf values in TLC, the melting points and the IR, NMR and mass spectra are perfectly analogous to those obtained after separation of the isomeric mixtures.

EXAMPLE 11

Antitumoral activity of the unoxidized chloroethylnitrosourea compounds according to the invention The oncostatic activity of these nitrosated derivatives was determined at the I.C.I.G. in VILLEJUIF (Department of Prof. MATHE) following a described experimental protocol: M. HAYAT et al., Cancer Chemother. Pharmacol., 1979, 3, 217–221; R. MARAL et al., Eur. J. Med. Chem., submitted for publication.

(a) Experimental protocol

Male B$_6$D$_2$F$_1$/OLA mice are inoculated intraperitoneally with 10$^5$ cells of the leukemia strain L1210 on day 0 and divided into groups. The first is the control group and the others are treated with the drugs at different concentrations on days 1, 5 and 9. The compounds are injected as a suspension in olive oil. The mortality of the animals is observed and the autopsy indicates whether it is due to leukemia or to the toxic action of the products.

The 50% lethal dose (LD$_{50}$ acute) is determined by taking into account the mortality which has occurred before the 8th day among the animals treated on day D:1. The survival median of the treated animals (mT) and the control animals (mC) was established and Wilcoxon's non-parametric statistical test was applied. The results are considered positive if the index I $$\left( I = \frac{mT}{mC} \times 100 \right)$$

is greater than 125 and the test Is significant at p≦0.05. The value ∞ indicates that 50% or more of the animals survive to day +60.

(b) Results

The greater the interval between doses for maximum efficacy, i.e. where I=∞, the more valuable is the product's activity on leukemia L1210.

We see in Table II that the isomeric mixture (8), consisting of S-methyl-N-[N-(2-chloroethyl)-N-nitrosocarbamoyl] cysteamine (3) and S-methyl-N-nitroso[N-N-chloroethyl)carbamoyl] cysteamine (sic) (4), although of low toxicity, does not exhibit any activity, As the major part of this mixture (3+4) consists of the compound with NO nearer the sulfur, this work was therefore directed towards molecules nitrosated nearer the chlorine. Three molecules appear to be of great interest, namely N-[N-(2-chloroethyl)-N-nitrosocarbamoyl]-cysteamine (1), S-methyl-N-[N-2-chloroethyl)-N-nitrosocarbamoyl]cysteamine (3) and S-acetyl-N-[N-

(2-chloroethyl)-N-nitrosocarbamoyl] cysteamine (5), which, although having LD$_5$O values ranging from 19 to 25 mg/kg, all have I indices at infinity. Furthermore, these three compounds are capable of giving a survival rate of 100% after 60 days, at different doses.

S-Trityl-N-[N-(2-chloroethyl)-N-nitrosocarbamoyl]-cysteamine (sic) (9) is not toxic as its LD$_{50}$ is greater than 625 mg/kg. Assessment of its activity is premature, however, because the results quoted are only partial.

tered in physiological serum. The mortality is recorded every day. The survival median was determined for the treated animals and the control animals. The results are considered to be positive if the index I=

$$\left( \frac{\text{survival median of the treated animals}}{\text{survival median of the control animals}} \times 100 \right)$$

TABLE II

ANTITUMORAL ACTIVITY, ON LEUKEMIA L.1210 i.p. IN MICE, OF THE UNOXIDIZED COMPOUNDS ACCORDING TO THE INVENTION (UNOXIDIZED ON THE SULFUR)

| Compounds | LD$_{50}$ mg/kg i.p. | DOSES mg/kg i.p. | DAYS | I = $\frac{T}{C}$ × 100 | % of ANIMALS SURVIVING to 60 DAYS |
|---|---|---|---|---|---|
| (1) ICIG 2016 | 19 | 15 | +1 | ∞ | 100 |
| | | 12.5 | 1,5,9 | ∞ | 100 |
| | | 10 | " | ∞ | 100 |
| | | 5 | " | ∞ | 100 |
| | | 2 | " | 188 | |
| | | 0.8 | " | 162 | |
| | | 0.32 | " | 265 | |
| (3) ICIG 2017 | 22 | 15 | 1,5,9 | 156 | 87 |
| | | 12.5 | " | ∞ | 100 |
| | | 5 | " | ∞ | |
| | | 2 | " | 158 | |
| | | 0.8 | " | 167 | |
| | | 0.32 | " | 133 | |
| (5) ICIG 2018 | 25 | 20 | 1,5,9 | 211 | 25 |
| | | 15 | " | 490 | 80 |
| | | 12.5 | " | ∞ | 100 |
| | | 10 | " | ∞ | 14 |
| | | 5 | " | 217 | |
| | | 4 | " | 158 | |
| | | 1.6 | " | 117 | |
| | | 0.64 | " | 100 | |
| (8) ICIG 1327 | 80 | 40 | 1,5 | 80 NS | |
| | | 16 | 1,5 | 100 NS | |
| (9)+ ICIG 2069 | >625 | 625 | 1,5,9 | >278 | |
| | | 250 | 1,5,9 | >278 | |

+ partial results
NS Not significant

EXAMPLE 12

Antitumoral activity of the sulfoxide derivatives (A$_1$/A$_2$) and sulfone derivatives (B$_1$/B$_2$) of the compounds according to the invention This activity was also studied on mice carrying leukemia L 1210 grafted i.p. This experimental tumor is the one most frequently used in the primary screening of cytostatic drugs.

These tests were conducted in parallel in two laboratories: at Unit 71 of the Institut National de la Santé et de la Recberche Médiecale (INSERM), ClermontFerrand, and at the Institut de Cancérologie et d' Immunogénétique (ICIG), Villejuif.

The antitumoral efficacy of the products according to the invention was compared with that of CNCC.

(a) Experimental protocol

On day D:0, three-month-old male B$_6$D$_2$F$_1$ mice received 10$^5$ cells of the leukemia strain L 1210 by intraperitoneal administration. The animals are divided up into groups of 8 to 10 animals for the control groups and 6 to 8 animals for the treated groups. On days D:1, D:5 and D:9, the animals receive the treatment at different doses by intraperitoneal or intravenous administration. The CNCC is administered as a suspension in olive oil. The products according to the invention are adminis- is greater than 125.

The value ∞ means that 50% to 100% of the animals have survived to day D:90.

(b) Results

α—Experiments carried out at Unit 71 of INSERM

The cytostatic activity oi the products according to the invention on leukemia L 1210 was evaluated on B$_6$D$_2$F$_1$/IFFA CREDO mice according to the protocol described previously.

Treatment by intraperitoneal administration

The following were administered intraperitoneally (i.p.): the mixture A$_1$A$_2$ in the following proportions: A$_1$ (70%) and A$_2$ (30%), or the mixture B$_1$B$_2$ in the same proportions, or CNCC at the following doses: 10 mg/kg, 20 mg/kg, 30 mg/kg, 40 mg/kg and 50 mg/kg. The results are given in Table II and invite the following remarks:

very good efficacy of the mixture A$_1$A$_2$ at doses of 20 mg/kg, 30 mg/kg and 40 mg/kg, and of the mixture B$_1$B$_2$ at doses of 20 mg/kg, 30 30 mg/kg, 40 mg/kg and 50 mg/kg. These mixtures have an interval between doses for maximum efficacy (IDME) comparable with, and for the mixture B$_1$B$_2$ even greater than, that of CNCC. Furthermore, the number of animals surviving to 90 days is greater among those which have received the products according to the invention than among those which have received CNCC.

Treatment by intravenous administration

The mixtures $A_1A_2$ and $B_1B_2$, in the proportions and doses used in (a), were administered intravenously (i.v.) into the caudal vein. Comparison with CNCC for this method of administration is impossible because of the insolubility of this compound in the solvents which allow intravenous administration. The results are given in Table III.

The mixture $A_1A_2$ is very active at doses of 30 mg/kg and 40 mg/kg. The IDME of the mixture $B_1B_2$ is greater (30 mg/kg, 40 mg/kg and 50 mg/kg).

β—Experiments carried out at ICIG

The cytostatic activity of $A_1$ and $A_2$ on leukemia L 1210 was evaluated on $B_6D_2F_1OLA$ mice at ICIG.

Treatment of the animals with the mixture $A_1A_2$ in the proportions of $A_1$ (70%) and $A_2$ (30%) gives results very comparable with those obtained at Unit 71 of INSERM (Table III).

ICIG also studied the antitumoral activity of each isomer $A_1$ and $A_2$, separately administered intravenously, on leukemia L 1210. The results are collated in Table IV and show a low activity of $A_1$ and a high activity of $A_2$ with the presence of an IDME and the achievement of a high percentage of mice surviving to day D:100. Comparison of the active doses with those of CNCC is impossible because of the insolubility of CNCC, as mentioned previously.

used so as to be able to make a comparison with CNCC. The mixture $A_1A_2$ and the CNCC were administered at equivalent doses and the plasma concentrations of $A_1$ and $A_2$ were measured as a function of time. cl (a) Experimental protocol A solution of the mixture $A_1A_2$ in distilled water is administered by stomach tube at a dose of 574 mg/m². A suspension of CNCC in olive oil is administered at a dose of 500 mg/m², also by stomach tube.

Preparation of the samples

The blood, taken by cardiac puncture, is centrifuged rapidly at 4° C. The plasma (1 ml) is deposited on a cartridge of Extrelut® and extraction is carried out with 6 ml of methylene chloride. After evaporation, the dry extract is taken up in 150 µl of methylene chloride for chromatographic analysis.

α—Chromatographic analysis

Analysis of the plasma extracts for measuring the concentrations of $A_1$ and $A_2$ was performed by high performance liquid chromatography using the following technology:

Column (40 cm×0.46 cm) Si 100 10 µm (Merck)
Detector: Pye Unicam spectrophotometer (Philips)λ250 nm.
Flow rate: 2 ml/minute.
Elution carried out by means of a linear gradient ranging from methylene chloride 99.6%/ethanol 0.4% to methylene chloride 95%/ethanol 5% in 15 minutes
Retention time: $A_1$ 18.7 minutes A20 minutes.

TABLE III

ANTITUMORAL ACTIVITY OF THE MIXTURES $A_1A_2$ AND $B_1B_2$ ON LEUKEMIA L 1210 GRAFTED i.p. IN MICE

| METHOD OF ADMINIS-TRATION | PROPORTIONS OF THE MIXTURE | DOSE MG/KG T/C × 100 | | | | |
|---|---|---|---|---|---|---|
| | | 10 | 20 | 30 | 40 | 50 |
| i.p. | $A_1$ 70% $A_2$ 30% | 300(2/6) | ∞(6/6) | ∞(6/6) | ∞(5/6) | 295(0/6) |
| | $B_1$ 70% $B_2$ 30% | 190(0/6) | ∞(5/6) | ∞(6/6) | ∞(6/6) | ∞(5/6) |
| | CNCC | 250(0/6) | ∞(6/6) | ∞(6/6) | ∞(3/6) | 125(0/6) |
| i.v. | $A_1$ 70% $A_2$ 30% | 170(0/6) | 270(0/6) | ∞(6/6) | ∞(6/6) | ∞(3/6) |
| | $B_1$ 70% $B_2$ 30% | 190(0/6) | 230(0/6) | ∞(6/6) | ∞(6/6) | ∞(5/6) |

Treatment $D_1$, $D_5$, $D_9$.

$T/C = \frac{\text{survival median of the treated animals}}{\text{survival median of the control animals}} \times 100$ ∞ = 50 to 100% of the animals surviving to 90 days
( ) = number of animals surviving to 90 days

TABLE IV

ANTITUMORAL ACTIVITY OF $A_1$ AND $A_2$, INJECTED SEPARATELY, ON LEUKEMIA L 1210 GRAFTED i.p. IN MICE

| METHOD OF ADMINIS-TRATION | PRODUCT | DOSE mg/kg T/C × 100 | | | | | | |
|---|---|---|---|---|---|---|---|---|
| i.v. | | 5 | 10 | 20 | 30 | 40 | 50 | 60 |
| | $A_1$ | 100 | 100 | 133 | 133 | 158 | 158 | toxic |
| | | 1 | 5 | 10 | 20 | 30 | 40 | — |
| | $A_2$ | 100 | ∞ | ∞ | 63 | 63 | 63 | |

EXAMPLE 13

Pharmacokinetic experiments:

The plasma absorption and clearance kinetics of the products $A_1$ and $A_2$ according to the invention were studied on different animal species after oral administration. A mixture $A_1A_2$ in the proportions 70%/30% was (b) Results The plasma concentrations of $A_1$ and $A_2$ after oral administration of either the mixture $A_1A_2$ or CNCC to mice, rats and rabbits are reported in Table V.

Whatever the animal species, the concentrations of $A_1$ and $A_2$ are much higher in the case of the administration of the products A₁ and A₂ according to the invention than in the case of the administration of CNCC. Measurement of the areas under the curves confirms these results.

These preliminary pharmacokinetic data tend to show that the plasma concentration of the active compound A₂ (cf. Example 12) is considerably greater in the case of the administration of A₁A₂ than in the case of the administration of CNCC.

The bioavailability of the products A₁ and A₂ according to the invention is therefore greater than that of CNCC.

-continued wherein n is 1 or 2.

3. A compound of the formula:

TABLE V

COMPARISON OF THE PLASMA CONCENTRATIONS OF A₁ AND A₂ AFTER p.o. ADMINISTRATION OF THE MIXTURE A₁A₂ AND THE EQUIVALENT DOSE OF CNCC

| PRODUCTS ADMINISTERED | ANIMAL | | NMOL/ML | 5 MIN | 15 MIN | 30 MIN | 45 MIN | 1 H | 1 H 30 MIN | 2 H | 3 H | 4 H 30 MIN |
|---|---|---|---|---|---|---|---|---|---|---|---|---|
| A₁A₂ | MICE | A₁ | 208.0 | 206.0 | 177.0 | 124.0 | 88.0 | 35.4 | 23.3 | 10.1 | 4.3 |
| CNCC | (n = 10) | A₂ | 83.0 | 81.5 | 66.3 | 43.7 | 29.9 | 10.8 | 6.3 | 2.9 | 0.9 |
|  |  | A₁ | 13.7 | 34.2 | 71.4 | 32.8 | 37.1 | 26.2 | 20.2 | 11.0 | 6.5 |
|  |  | A₂ | 5.3 | 13.2 | 35.7 | 16.5 | 19.0 | 12.7 | 9.9 | 6.7 | 3.5 |
| A₁A₂ | RATS | A₁ | 22.3 | 42.4 | 52.9 | 33.9 | 32.9 | 29.2 | 15.7 | 7.3 | — |
| CNCC | (n = 5) | A₂ | 8.5 | 17.7 | 22.5 | 11.4 | 14.2 | 12.9 | 7.8 | 2.9 | — |
|  |  | A₁ | 2.8 | 8.0 | 12.0 | 14.8 | 18.4 | 20.3 | 12.7 | 11.1 | 3.9 |
|  |  | A₂ | 0.9 | 3.2 | 5.4 | 7.2 | 8.1 | 11.4 | 6.4 | 6.5 | 2.2 |
| A₁A₂ | RABBITS | A₁ | 26.7 | 28.5 | 41.0 | 39.2 | 39.4 | 27.0 | 19.4 | 10.6 | 3.8 |
| CNCC | (n = 5) | A₂ | 11.0 | 11.7 | 16.5 | 15.0 | 14.2 | 9.2 | 6.3 | 2.9 | 0.7 |
|  |  | A₁ |  | 5.0 | 9.4 | 10.6 | 10.0 | 8.6 | 7.4 | 4.7 | 2.8 |
|  |  | A₂ |  | 1.8 | 5.0 | 6.0 | 5.5 | 4.2 | 3.5 | 2.0 | 1.0 |

What is claimed is:

1. A compound selected from the group consisting of:

2. An isomeric mixture of the formulae:

or their isomeric mixture.

4. A pharmaceutical composition comprising a tumor-inhibiting amount of one or more of the compounds from the group consisting of:

and a pharmaceutically acceptable carrier.

* * * * *

UNITED STATES PATENT AND TRADEMARK OFFICE
CERTIFICATE OF CORRECTION

PATENT NO. : 5,001,158
DATED : Mar. 19, 1991
INVENTOR(S) : Madelmont, et al It is certified that error appears in the above-identified patent and that said Letters Patent is hereby corrected as shown below:

On the title page, items [54], [75], [73], and [30] should be corrected as follows:

(54) NITROSOUREAS COMPOUNDS PREPARATION THEREOF AND UTILIZATION THEREOF IN ANTICANCEROUS CHEMIOTHERAPY (75) Inventors: Jean-Claude Madelmont, Romagnat;
Denise Godeneche, Chamalieres;
Marie-France Moreau, Romagnat;
Daniel Parry, Beaumont;
Gaston Meyniel, Clerrint;
Joel Oiry; Jean-Louis Imbach,
both of Montpellier, all of France (73) Assignee: Centre National De La Recherche Scientifique;
Institut National De La Sante Et De La Recherche Medicale (30) Foreign Application Priority Data April 11, 1984 (FR) France ........84 05733

Signed and Sealed this

Second Day of March, 1993

*Attest:*

STEPHEN G. KUNIN

*Attesting Officer*    *Acting Commissioner of Patents and Trademarks*